US010002419B2

(12) United States Patent
Rapaka et al.

(10) Patent No.: US 10,002,419 B2
(45) Date of Patent: Jun. 19, 2018

(54) DIRECT COMPUTATION OF IMAGE-DERIVED BIOMARKERS

(71) Applicant: Siemens Healthcare GmbH, Erlangen (DE)

(72) Inventors: Saikiran Rapaka, Pennington, NJ (US); Puneet Sharma, Monmouth Junction, NJ (US); Atilla Peter Kiraly, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 201 days.

(21) Appl. No.: 14/639,189

(22) Filed: Mar. 5, 2015

(65) Prior Publication Data

US 2016/0260208 A1 Sep. 8, 2016

(51) Int. Cl.
*G06T 7/00* (2017.01)
*G06T 7/143* (2017.01)
*G06T 7/11* (2017.01)
*A61B 6/00* (2006.01)
*G06K 9/00* (2006.01)
*G06K 9/32* (2006.01)
*A61B 6/03* (2006.01)

(52) U.S. Cl.
CPC ............ *G06T 7/0012* (2013.01); *A61B 6/503* (2013.01); *A61B 6/504* (2013.01); *A61B 6/507* (2013.01); *A61B 6/5217* (2013.01); *G06K 9/00201* (2013.01); *G06K 9/3233* (2013.01); *G06T 7/11* (2017.01); *G06T 7/143* (2017.01); *A61B 6/032* (2013.01); *G06K 2209/05* (2013.01); *G06T 2207/30048* (2013.01); *G06T 2207/30104* (2013.01); *G06T 2210/41* (2013.01)

(58) Field of Classification Search
CPC ... G06T 7/0012; G06T 7/0087; G06T 7/0081; G06T 2207/30104; G06T 2207/30048; G06T 2210/41; G06K 9/00201; G06K 9/3233; G06K 2209/05; A61B 6/03
See application file for complete search history.

(56) References Cited

U.S. PATENT DOCUMENTS

2005/0059876 A1* 3/2005 Krishnan ............... G06T 7/0012
600/407
2010/0296709 A1* 11/2010 Ostrovsky-Berman . G06T 7/162
382/128
(Continued)

FOREIGN PATENT DOCUMENTS

WO WO2005114229 A2 12/2005

OTHER PUBLICATIONS

Antiga, Luca, et al. "An image-based modeling framework for patient-specific computational hemodynamics." Medical & biological engineering & computing 46.11 (2008): 1097-1112.*
(Continued)

*Primary Examiner* — Bhavesh Mehta
*Assistant Examiner* — Menatoallah Youssef

(57) ABSTRACT

A method for computing image-derived biomarkers includes receiving image data defining a three-dimensional image volume representative of an anatomical region of interest. Features characterizing local variations of intensity in the image data using an intensity model are identified. The features are used to perform one or more modeling computations directly on the image data to derive information related to a biomarker of interest.

21 Claims, 4 Drawing Sheets

(56) References Cited

U.S. PATENT DOCUMENTS

2012/0041318 A1 2/2012 Taylor
2014/0003701 A1* 1/2014 Masood .............. G06T 7/0012
382/134

OTHER PUBLICATIONS

Law, Wai Kong, and Albert CS Chung. "Segmentation of vessels using weighted local variances and an active contour model." 2006 Conference on Computer Vision and Pattern Recognition Workshop (CVPRW'06). IEEE, 2006.*
Huo, Yunlong, et al. "A validated predictive model of coronary fractional flow reserve." Journal of the Royal Society Interface 9.71 (2012): 1325-1338.*
Chung, Albert CS. "Image Segmentation Methods for Detecting Blood Vessels in Angiography." ICARCV. 2006.) in view of Law (Law, Wai Kong, and Albert CS Chung. "Segmentation of vessels using weighted local variances and an active contour model." 2006 Conference on Computer Vision and Pattern Recognition Workshop (CVPRW'06). IEEE, 2006.*
Mihalef Viorel et al: "Model-Based Estimation of 4D Relative Pressure Map from 4D Flow MR Images", Network and Parallel Computing; [Lecture Notes in Computer Science; Lect.Notes Computer], Springer International Publishing, Cham, pp. 236-243, Sep. 26, 2013.
Donati Fabrizio et al: "Pressure mapping from flow imaging: Enhancing computation of the viscous term through velocity reconstruction in near-wall regions". 2014 36th Annual International Conference of the IEEE Engineering in Medicine and Biology Society, IEEE, pp. 5097-5100, Aug. 26, 2014.

* cited by examiner

US 10,002,419 B2

DIRECT COMPUTATION OF IMAGE-DERIVED BIOMARKERS

TECHNICAL FIELD

The present disclosure relates generally to computation of biomarkers using a model directly applied to image data. The disclosed systems, methods, and apparatuses, may be applied, for example, to modeling biomarkers based on 3D image data.

BACKGROUND

Traditionally, medical imaging has focused on providing an accurate geometric description of the anatomical structures being imaged. Recent studies have highlighted the power of medical images towards obtaining functional quantification of organ behavior. Some notable examples are the ability to non-invasively compute blood pressures from images, ability to compute strain and stress in biological tissues and models to detect irregularities in electrical signal propagation in cardiac arrhythmias. These models combine the anatomic information obtained from medical images with models derived from physics to provide significant insight into the patient's pathology.

A drawback of the aforementioned conventional techniques is that a detailed organ segmentation must be used as an input to compute the relevant biomarkers. Typically, a segmentation operation is performed as an intermediary step between imaging and modeling. During this operation, a segmented mesh is created based on the imaging data. Then, this mesh is used as input into the computational models. The segmentation operation is frequently the source of much uncertainty and inter-user variability. Further, it is typically an effort-intensive process requiring much attention. For example, the time required to perform the segmentation operation is often equal to, if not greater than, the time required to execute the computational model. Accordingly, it is desired to create a technique for deriving biomarkers without prior segmentation.

SUMMARY

Embodiments of the present invention address and overcome one or more of the above shortcomings and drawbacks, by providing methods, systems, and apparatuses related to the direct application of modeling techniques to image data, without requiring a prior segmentation. The proposed schemes may be used, for example, to reduce the processing time involved with deriving modeling results.

According to some embodiments, a method for computing image-derived biomarkers includes receiving image data defining a three-dimensional image volume representative of an anatomical region of interest. This image data may comprise, for example, voxels and the features characterizing local variations of intensity are identified on a per-voxel basis. In some embodiments, the anatomical region of interest comprises cardiac vascular structure. Features characterizing local variations of intensity in the image data using an intensity model are identified. The features are used to perform one or more modeling computations directly on the image data to derive information related to a biomarker of interest. In some embodiments, these modeling computations provide a measure of fluid dynamics within the cardiac vascular structure. The measure of fluid dynamics may correspond to, for example, pressure difference or fractional flow reserve within the cardiac vascular structure. In some embodiments, a plurality of weighting values corresponding to the plurality of voxels is derived using the features characterizing local variations of intensity and incorporated into the modeling computations.

In some embodiments of the aforementioned method, an approximate segmentation of the anatomical region of interest is generated based on results of performing the one or more modeling computations. In some embodiments, this segmentation is a binary mask. In other embodiments, the approximate segmentation is a gray-level mask representative of segmentation accuracy for the anatomical region of interest. In one embodiment, the approximate segmentation comprises a probability of particular pixels in the three-dimensional image volume belonging to the anatomical region of interest. The approximate segmentation may be used, for example, to iteratively perform the one or more modeling computations directly on the image data to derive information related to the biomarker of interest. In some embodiments, the approximate segmentation is refined during each iteration based on results of the one or more modeling computations.

According to other embodiments, a second method for computing image-derived biomarkers includes receiving image data comprising a plurality of voxels defining a three-dimensional image volume representative of an anatomical region of interest. An anatomical structure related to a biomarker of interest is determined, for example, by selecting the anatomical structure and the biomarker of interest based on the medical condition (e.g., specified by user-input). An intensity model is selected based on the anatomical structure related to the biomarker of interest. For example, in one embodiment, the intensity model is selected based on a database of past history from other patients and annotated models for how different intensity values correspond to presence of the anatomical structure. The intensity model is used to determine a plurality of weighting values, with each respective weighting value corresponding to a respective voxel included in the image data. A computational model is applied to the image data using the plurality of weighting values to derive information related to the biomarker of interest.

Various features may be added, enhanced, and/or refined in the aforementioned second method. For example, in some embodiments, one or more study-specific input values defining seed points for the intensity model are determined and used by the intensity model in determining the weighting values. In one embodiment, the study-specific input values are automatically selected based on previous studies related to the anatomical structure. In another embodiment, the study-specific input values are determined based on user input via a graphical user interface (GUI). In some embodiments, an approximate segmentation of the anatomical structure is generated based on results of applying the computational model to the image data. This approximate segmentation may be, for example, a binary mask or a gray-level mask representative of segmentation accuracy for the anatomical region of interest. In some embodiments, the approximate segmentation is used to iteratively apply the computational model to the image data. The approximate segmentation may be refined during each iteration based on results of applying the computational model to the image data.

According to other embodiments, a system for computing image-derived biomarkers includes a scanner device and a computer. The scanner device is configured to acquire image data defining a three-dimensional image volume representative of an anatomical region of interest. The computer is operably coupled to the scanner device and configured to identify intensity differences in the image data using an intensity model, and to use the intensity differences in the image data to apply a computational model directly to the image data to derive information related to a biomarker of interest.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION

The following disclosure describes the present invention according to several embodiments directed at methods, systems, and apparatuses for computing relevant biomarkers by acting directly on the image (e.g., via a voxel grid), without requiring the intermediate step of creating a segmented mesh. Briefly, an intensity model is used to identify a region of interest in the image data. The computational model is then applied across the image, using the output of the intensity model to guide calculations related to the biomarker. Conceptually, this may be viewed as drawing a box around the area of interest (e.g., an artery which is twisted) and performing computations across the entire box. Conventional models first try to get the shape of the vessel itself and then run the model inside of the vessel. However, with various embodiments described herein, the vessel is not separated, rather the modeling equations are applied across the entire box, and the equations of the computational model are weighted differently based on whether a particular region of the box appears to be vessel or not. In some embodiments, the user may specify features such as, without limitation, the start and end points of interest in a vascular network, or regions near a valve where total stress or strain information is needed. In some embodiments, additional parameters may also be computed using image-derived quantities. The various methods, systems, and apparatuses are especially applicable to the cardiac applications where modeling analysis has traditionally required segmentation of the heart. However, it should be understood that the techniques described herein may be generally applied to the analysis of any type of anatomical structure.

Figure 1:
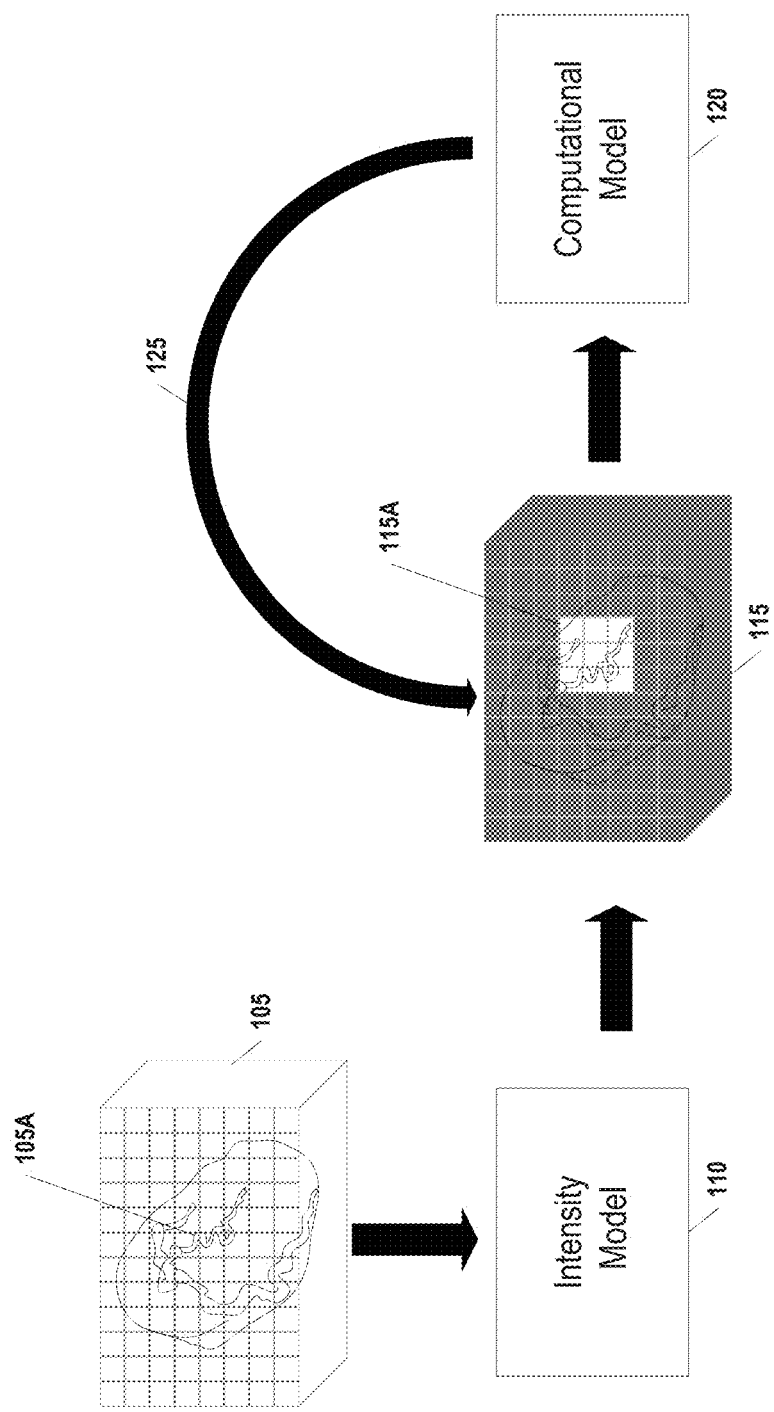
FIG. 1 provides a high-level illustration of the direct application of modeling techniques to image data, without requiring a prior segmentation, according to some embodiments of the present invention.

FIG. 1 provides a high-level illustration of the direct application of modeling techniques to image data, without requiring a prior segmentation, according to some embodiments of the present invention. A 3D Image Volume 105 is acquired using one or more imaging devices known in the art such as, for example, a Magnetic Resonance Imaging (MRI) or Computed Tomography (CT) scanner. It should be noted that the general techniques discussed herein may be applied directly on the imaging device or at a workstation as a post-processing step. Thus, in some embodiments, a computer that is part of the imaging device (i.e., operably coupled to the scanner acquiring the imaging data) may be configured to perform the techniques described herein. In other embodiments, the 3D Image Volume 105 can be stored on a database (not shown in FIG. 1) and retrieved at the workstation any time after imaging. In the example of FIG. 1, the 3D Image Volume 105 provides a representation of a heart. The user in this example desires to analyze a potential blockage in a vessel 105A included in the heart by analyzing one or more biomarkers. In this context of this disclosure, the term biomarker refers to any measurable anatomical substance or behavior which may be indicative of the severity or presence of a phenomenon such as disease, infection, or environmental exposure.

An Intensity Model 110 identifies a region of interest in the 3D Image Volume 105 where the biomarker is expected to be present based on differences in image intensity and its variations between individual voxels of the Image Volume 105. The result of the Intensity Model 110 is to introduce homogenized approximations of the effect of internal boundaries without prior segmentation. The Intensity Model 110 may be applied across the voxels of the 3D Image Volume 105 to assign a likelihood of each voxel belonging to anatomical features related to the biomarker. In some embodiments, the Intensity Model 110 is applied on a per-voxel basis while, in other embodiments, it characterizes broad regions like an entire section of tissue. The data analyzed by the Intensity Model 110 may include, for example, local image intensities, gradients, and/or the correlation structure in the 3D Image Volume 105. The Intensity Model 110 may be implemented, for example, using one or more machine learning techniques known in the art. For example, in one embodiment, a Bayesian Classifier is trained using intensity features and/or spatial features present in previously acquired image data. This Bayesian Classifier may then be used to identify the features in the 3D Image Volume 105. In FIG. 1, the output of the Intensity Model 110 is illustrated by 3D Image Volume 115 with Region of Interest 115A.

It should be noted that the Intensity Model 110 is only one example of a model that may be applied to identify the Region of Interest 115A. In some embodiments, in addition to (or as an alternative to) the Intensity Model, other imaging modalities may be used. For example, in the 3D space, other functional information such as tissue density and/or rigidity may be used as part of the modeling analysis.

Once the Region of Interest 115A has been identified, a Computational Model 120 model is launched directly on the 3D Image Volume 115 using the obtained parameters defining the Region of Interest 115A. The equations used by the Computational Model 120 include weighting terms (described in greater detail below) corresponding to features of the Region of Interest 115A, which allow the equations to be run over the entire voxel grid.

As an example, consider an embodiment where the Computational Model 120 is designed for hemodynamic flow modeling using computational fluid dynamics. It would not be necessary for the user to segment the vessel walls. The model utilizes local image intensity and its variations to direct the computations towards the desired biomarker. One such model could be the use of forces acting on the fluid flow depending on the local image intensity variations. This is a homogenized representation which models the drag effect of the presence of un-modeled walls and prevents leakage of blood from the fluid domain. The mathematical formulation for the fluid flow applied by the Computational Model 120 may be determined by:

$$\rho\left(\frac{\partial u}{\partial t} + \nabla \cdot uu\right) = -\nabla p + \mu \nabla^2 u + F \qquad (1)$$

where, u is the blood velocity, p is the blood pressure, $\rho$ and $\mu$ are the blood density and viscosity respectively. The term F is the force which applies the drag effect, allowing the area to be modeled without prior segmentation. This force F may be modeled, for example, by the following equation:

$$F = -\frac{\mu}{\alpha}u - \frac{1}{2}C_2\rho|u|u \qquad (2)$$

where $\alpha$ and $C_2$ represent local effective material properties which depend on the image intensity and its local variations. The terms $\alpha$ and $C_2$ may be selected so as to establish that most of the flow is in the vascular network. The forces are taken to be negative in velocity, since the force acts to retard the flow, acting as a drag term. For example, if $C_2$ is a small value then there is little drag (e.g., in the vessel). Alternatively, if $C_2$ is large there is a lot of drag (e.g., in tissue). In representation of F presented above, it is possible to use only the linear part of the force model (Darcy's law), just the quadratic term (Forchheimer's law) or a combination of both of these terms.

Although Equations 1 and 2 set out above are directed to measure flow, the general concept may be extended to other clinical applications. For example, if analyzing the electrical propagation on the heart, the electrical properties for the tissue are so designed such that the action potential driving the heart's motion does not go outside of the myocardial tissue. Additionally, if an approximate segmentation were available (e.g., either as a binary or gray-level mask, or as an approximate mesh), the Computational Model 120 may utilize this information to guide the modeling computations. Note that the mask may be statistical, conveying the likelihood of the segmentation correctness. Additionally, it should be noted that Equations 1 and 2 are merely one example of the mathematical formulation for the fluid flow applied by the Computational Model 120. Other equations may be used in different embodiments, for example, without using a segmentation.

In some embodiments, the predictions generated using the techniques described herein may be used to guide a segmentation. Thus, the various embodiments discussed herein may be used in conjunction with existing models that depend on segmented mesh for input. For example, by the magnitudes of flow velocities and other hemodynamic quantities through a particular vessel using the techniques described herein, the features of the vessel (e.g., location of the walls) can be more accurately identified and depicted in a segmented mesh than by just analyzing the shape of the vessel alone. This segmentation may be refined by iteratively applying the Computational Model 120 to refined anatomical features, as illustrated by the arrow 125 in FIG. 1. This provides one difference between the techniques described herein and the conventional techniques, which assume that geometry of the segmentation is fully accurate and there is no feedback in the process that allows for correction. The choice of whether to perform calculations iteratively may depend, for example, on the need for an exact geometry of the anatomy for further processing (e.g., in the case of stent planning). During each iteration, the modeled values (e.g., pressure) are analyzed to determine how much they change. Once the change between iterations is below a threshold value, iterations can stop. However, the criteria for the number of iterations can also (or alternatively) depend on other conditions specific to the problem. Moreover, if the main goal is to get segmentation, one doesn't need to solve flow exactly. For example, in some embodiments, a reduced model with simplified equations may be used to allow for faster execution of the iterations of the modeling process.

In some embodiments, multiple images (from a single modality or from multiple modalities) may be combined to determine image features/properties that are used in the physical computation performed by the Computational Model 120. For example MR and CT images may be combined to obtain properties of soft tissue, which are then used by the Computational Model 120 in performing the physical computations.

It should also be noted that, although the example described above is directed at hemodynamic flow modeling the techniques described herein are generally applicable to the modeling of various types and forms of anatomical behavior. For example, consider the various modeling that may be performed on heart imaging data. Electrophysiology models may be used to analyze the electrical conduction patterns on the heart to determine whether these patterns are operating in a synchronous manner or whether some potential heart defect is occurring. Mechanical models may be used to analyze the various stresses and strains on the heart and determine how well it is pumping. Additionally, models may be used to capture the dynamics of the blood flow in vessels. In all of these cases, the techniques described herein may be used to model the relevant data without the exact shape of the heart in a segmented form. Rather, the model can directly operate on voxel data, a mask, or a probabilistic representation of underlying components (e.g., atria, ventricles, vessels, etc.) without creating the segmented shape of the organ.

Figure 2:
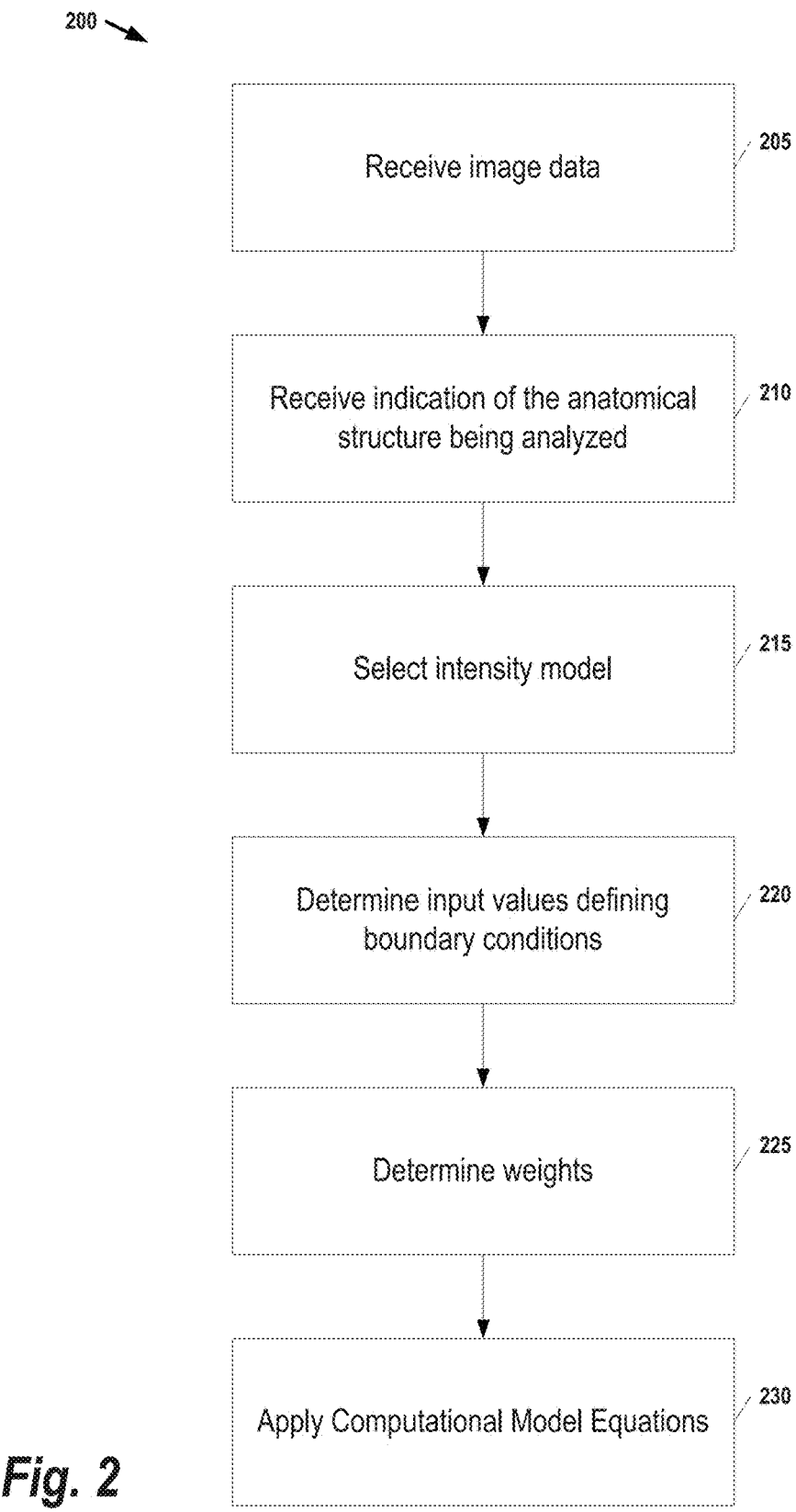
FIG. 2 provides a flow chart illustrating a process for computing biomarkers directly using 3D image data, according to some embodiments of the present invention.

FIG. 2 shows a flowchart illustrating a process 200 for computing biomarkers, according to some of the embodiments described herein. In some embodiments, this process 200 is performed at an imaging device during or after image reconstruction. In other embodiments, this process 200 is performed at a workstation as a post-processing step after imaging is complete. At 205, 3D image data comprising a voxel grid is received directly or indirectly from an imaging device. Any type of imaging device known in the art may be used in acquiring the image data including, without limitation, various types of MRI and CT devices.

Beginning at 210, a mapping process is performed to apply a predetermined intensity model to the acquired 3D image data. At 210, an indication of what anatomical structure is being measured is received based on, for example, user input. For example, continuing with the hemodynamic flow modeling example provided above, the user may indicate that he or she desires to measure pressure across a particular heart vessel. Alternatively, the user may simply specify a medical condition and the anatomical area of interest (any related biomarkers) may be automatically identified based on, for example, predetermined information which associates medical conditions with anatomical and biomarker data.

Next, at 215 in FIG. 2, an intensity model is selected based on the anatomical structure of interest. The intensity model, in its simplest form, just tells one where the modeled activity (e.g., flow) is expected to occur based on different image intensity values presented in the received 3D image volume. In some embodiments, this intensity model derived dynamically, while in other embodiments it is pre-determined and retrieved from a database. For example, in some embodiments, the intensity model is selected based on a database of past history from other patients and annotated models for how different intensity values correspond to the presence of a vessel or not. Additionally, in some embodiments, a patient's medical record can be used to identify what type of feature is being sought out for modeling. For example, if a patient has ongoing chest pain, the selection of the intensity model may be designed to identify potential blockages and focus on that area to see how best to adapt the model there.

Continuing with reference to FIG. 2, at 220, one or more study-specific input values to the intensity model are determined. For example, if the user is performing a pressure study of a vessel, these additional inputs may include boundary regions defining the ingress and egress seed points of the flow being measured. In some embodiments, these seed points are determined based on past biomarker calculations involving similar parameters. For example, continuing with the example of a study of pressure through a vessel, the seed points may be selected based on information used for similar studies applied to the same patient or other patients in the past. In other embodiments, the seed points may be derived using guidelines provided by organizations such as the American Heart Association (AHA). For example, AHA guidelines may define an average position for the vessel and the seed points may be defined by subtracting a particular value (e.g., defined in centimeters or millimeters) around that position. Alternatively, or if other data is unavailable, the seed points may be estimated with or without additional input from the user. For example, in some embodiments, the user interacts with a graphical user interface (GUI) to click on seed points defining the area of interest. Furthermore, it should be understood that the aforementioned techniques for defining seed points may also be used in combination. For example, in some embodiments, seed points may be automatically determined based on AHA guidelines. Then, these seed points may be adjusted by the user through interaction with the GUI. In addition, to input values defining the boundary conditions, other inputs may be determined to provide further guidance for the study. For example, another input to the model may be the amount of flow through the vessel (e.g., 5 ml/sec). This may be determined, for example, based on known ranges for flow amounts, the estimated dimensions of the vessel itself, and/or other patient data.

Once the intensity model is selected and its input values are determined, at 225 a plurality of weights are calculated using the intensity model. Weights can be calculated on a per-voxel or per-vertex basis, depending on the model used. In some embodiments, the weights associated with the particular voxel (or vertex) are determined based on both data associated with a particular voxel, as well as neighborhood and higher order information. For example, consider the simplest case where each voxel is 0 or 1 (i.e., a black and white image). The data includes the fact that a particular voxel is 1, it may also include an indication of how many neighbors are 1, what sort of curvature is there to the voxels with 1 values, the direction of the image gradient, etc. Using this information, a value may be determined that reflects the probability that the particular voxel is inside or outside the anatomical structure of interest.

At 230, the calculated weights are used to apply a computational model directly to the 3D image volume. In principle, model calculation is performed across the entire 3D image volume. However, the equations used by the model are designed to use the weights to ensure that almost none of the modeled activity (e.g., flow) takes place outside the area defined by the seed points derived at 220. For example, in some embodiments, the weights may be used to define a force value that is strong if the flow is going through what appears to be a vessel and that provides a lot of resistance for flow in areas that appear to be tissue. Thus, even if flow is started throughout the entire region, almost nothing goes through the tissue because there is too much force to overcome.

The process 200 illustrated in FIG. 2 may include one or more loops (not shown in FIG. 2) to iteratively apply the computational model directly to the 3D image volume. In some embodiments, an approximate segmentation of the anatomical region of interest is based on results of computational model applied at 230. This approximate segmentation may be, for example, a binary mask or a gray-level mask representative of segmentation accuracy for the anatomical region of interest. The approximate segmentation may be used to refine the approximate segmentation during each iteration based on results of the computational model. It should also be noted that the approximate segmentation may be used in additional computational processes unrelated to the model. Thus, the process 200 can be used in conjunction with conventional processes which depend on a segmented image for execution.

In some embodiments, the process 200 may be refined to reduce the processing time of the model. For example, anatomy outside of the seed points may also be excluded from the flow calculations or the 3D image volume may be cropped to just include a region of interest at any point of the process 200 prior to applying the computational model at 230.

Figure 3:
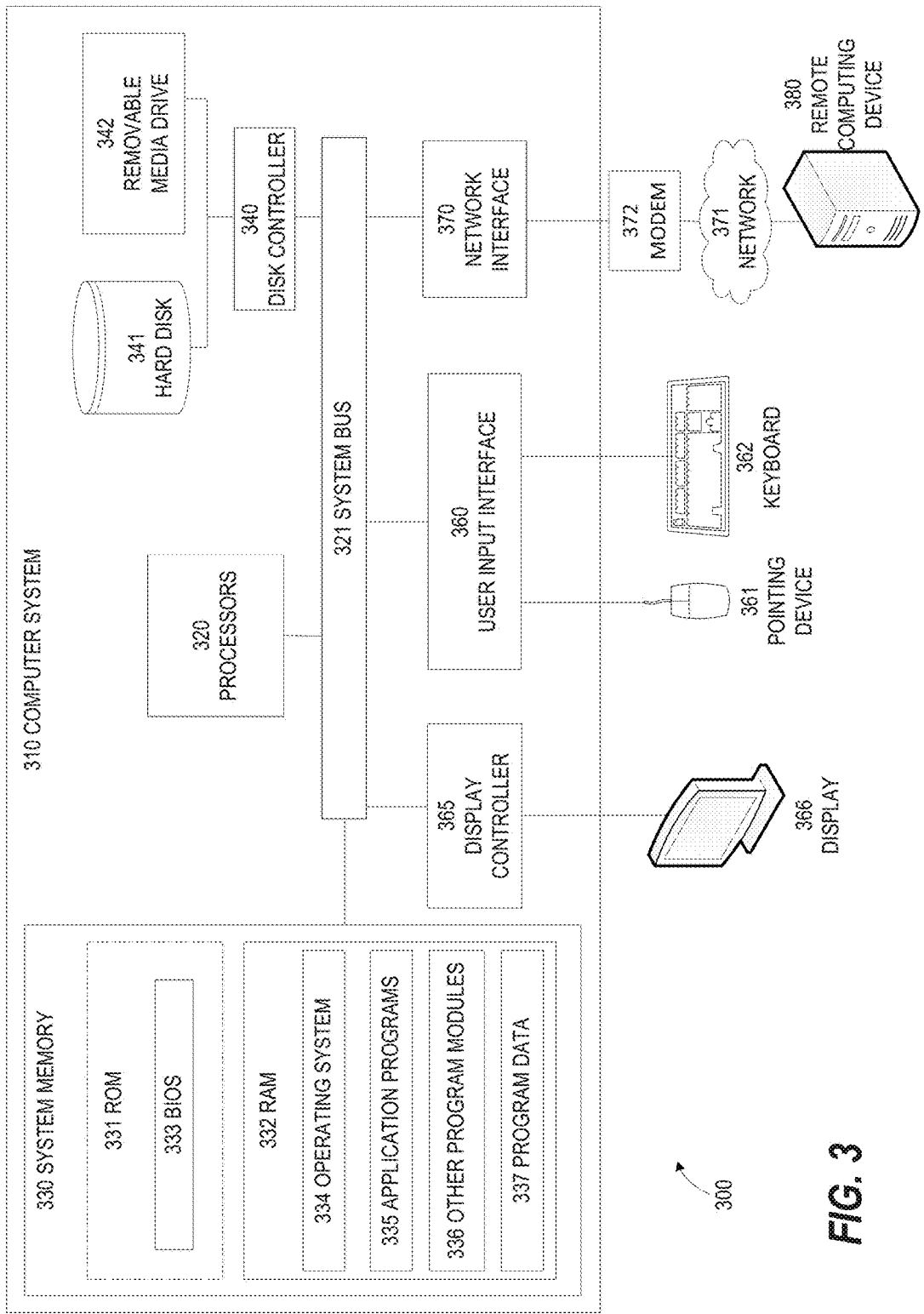
FIG. 3 illustrates an exemplary computing environment within which embodiments of the invention may be implemented.

FIG. 3 illustrates an exemplary computing environment 300 within which embodiments of the invention may be implemented. For example, this computing environment 300 may be used to implement the process 200 described in FIG. 2. The computing environment 300 may include computer system 310, which is one example of a computing system upon which embodiments of the invention may be implemented. Computers and computing environments, such as computer system 310 and computing environment 300, are known to those of skill in the art and thus are described briefly here.

As shown in FIG. 3, the computer system 310 may include a communication mechanism such as a bus 321 or other communication mechanism for communicating information within the computer system 310. The computer system 310 further includes one or more processors 320 coupled with the bus 321 for processing the information. The processors 320 may include one or more central processing units (CPUs), graphical processing units (GPUs), or any other processor known in the art.

The computer system 310 also includes a system memory 330 coupled to the bus 321 for storing information and instructions to be executed by processors 320. The system memory 330 may include computer readable storage media in the form of volatile and/or nonvolatile memory, such as read only memory (ROM) 331 and/or random access memory (RAM) 332. The system memory RAM 332 may include other dynamic storage device(s) (e.g., dynamic RAM, static RAM, and synchronous DRAM). The system memory ROM 331 may include other static storage device (s) (e.g., programmable ROM, erasable PROM, and electrically erasable PROM). In addition, the system memory 330 may be used for storing temporary variables or other intermediate information during the execution of instructions by the processors 320. A basic input/output system 333 (BIOS) containing the basic routines that help to transfer information between elements within computer system 310, such as during start-up, may be stored in ROM 331. RAM 332 may contain data and/or program modules that are immediately accessible to and/or presently being operated on by the processors 320. System memory 330 may additionally include, for example, operating system 334, application programs 335, other program modules 336 and program data 337.

The computer system 310 also includes a disk controller 340 coupled to the bus 321 to control one or more storage devices for storing information and instructions, such as a hard disk 341 and a removable media drive 342 (e.g., floppy disk drive, compact disc drive, tape drive, and/or solid state drive). The storage devices may be added to the computer system 310 using an appropriate device interface (e.g., a small computer system interface (SCSI), integrated device electronics (IDE), Universal Serial Bus (USB), or FireWire).

The computer system 310 may also include a display controller 365 coupled to the bus 321 to control a display 366, such as a cathode ray tube (CRT) or liquid crystal display (LCD), for displaying information to a computer user. The computer system includes an input interface 360 and one or more input devices, such as a keyboard 362 and a pointing device 361, for interacting with a computer user and providing information to the processor 320. The pointing device 361, for example, may be a mouse, a trackball, or a pointing stick for communicating direction information and command selections to the processor 320 and for controlling cursor movement on the display 366. The display 366 may provide a touch screen interface which allows input to supplement or replace the communication of direction information and command selections by the pointing device 361.

The computer system 310 may perform a portion or all of the processing steps of embodiments of the invention in response to the processors 320 executing one or more sequences of one or more instructions contained in a memory, such as the system memory 330. Such instructions may be read into the system memory 330 from another computer readable medium, such as a hard disk 341 or a removable media drive 342. The hard disk 341 may contain one or more datastores and data files used by embodiments of the present invention. Datastore contents and data files may be encrypted to improve security. The processors 320 may also be employed in a multi-processing arrangement to execute the one or more sequences of instructions contained in system memory 330. In alternative embodiments, hardwired circuitry may be used in place of or in combination with software instructions. Thus, embodiments are not limited to any specific combination of hardware circuitry and software.

As stated above, the computer system 310 may include at least one computer readable medium or memory for holding instructions programmed according embodiments of the invention and for containing data structures, tables, records, or other data described herein. The term "computer readable medium" as used herein refers to any medium that participates in providing instructions to the processor 320 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 341 or removable media drive 342. Non-limiting examples of volatile media include dynamic memory, such as system memory 330. Non-limiting examples of transmission media include coaxial cables, copper wire, and fiber optics, including the wires that make up the bus 321. Transmission media may also take the form of acoustic or light waves, such as those generated during radio wave and infrared data communications.

The computing environment 300 may further include the computer system 310 operating in a networked environment using logical connections to one or more remote computers, such as remote computer 380. Remote computer 380 may be a personal computer (laptop or desktop), a mobile device, a server, a router, a network PC, a peer device or other common network node, and typically includes many or all of the elements described above relative to computer system 310. When used in a networking environment, computer system 310 may include modem 372 for establishing communications over a network 371, such as the Internet. Modem 372 may be connected to bus 321 via user network interface 370, or via another appropriate mechanism.

Network 371 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 310 and other computers (e.g., remote computer 380). The network 371 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 371.

Figure 4:
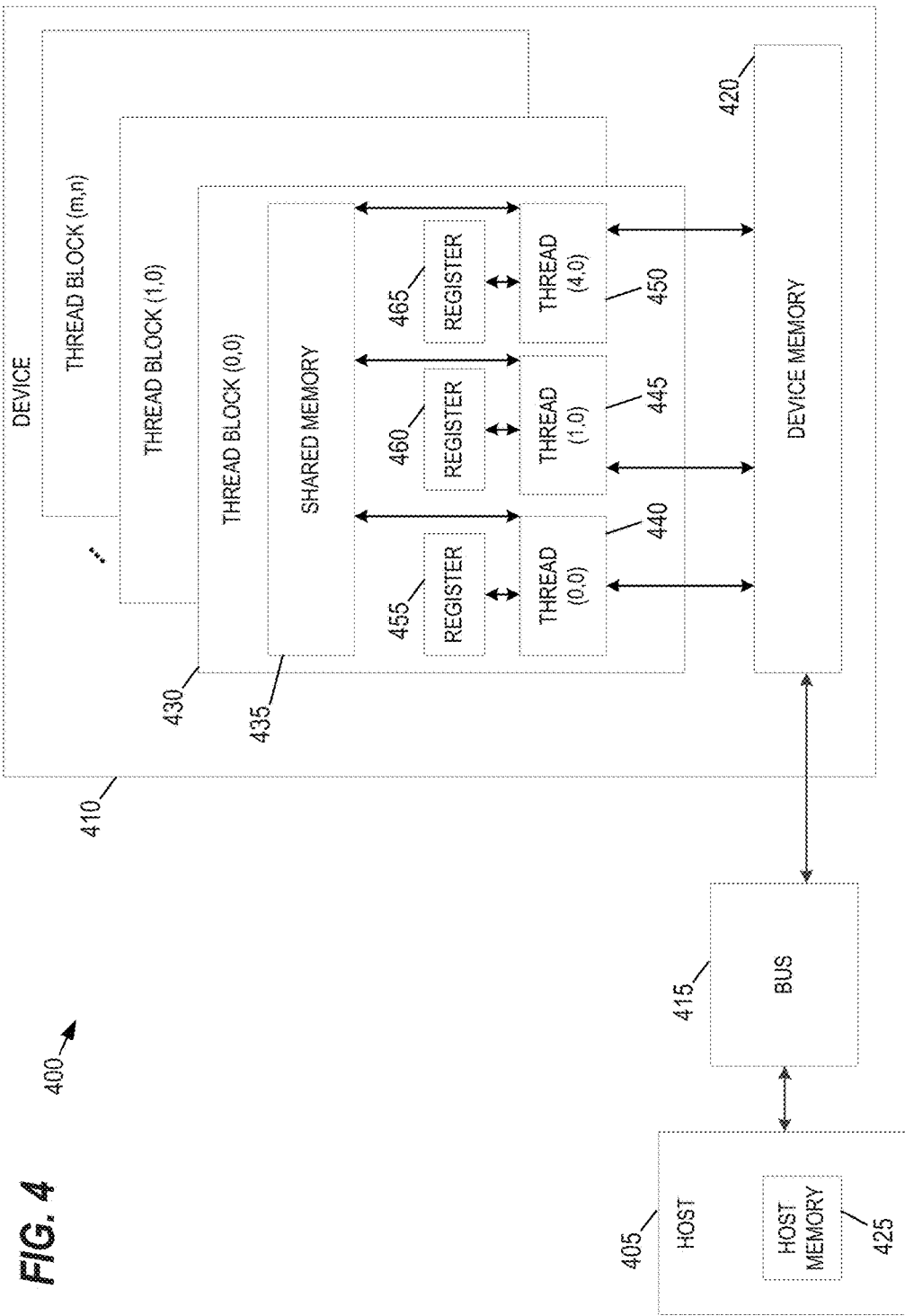
FIG. 4 provides an illustration of the parallel processing platform 400 that may be utilized to accelerate execution of the computational model, according to some embodiments.

FIG. 4 provides an illustration of the parallel processing platform 400 that may be utilized to accelerate execution of the computational model (see, e.g., Computational Model 120 in FIG. 1), according to some embodiments. This platform 400 may be used, for example, for implementations of the present invention where NVIDIA™ CUDA (or a similar parallel computing platform) is used. The architecture illustrated in FIG. 4 includes a host computing unit ("host") 405 and a GPU device ("device") 410 connected via a bus 415 (e.g., a PCIe bus). The host 405 includes the CPU (not shown in FIG. 4) and host memory 425 accessible to the CPU. The graphical processing device 410 includes the GPU and its associated memory 420, referred to herein as device memory. The graphical processing device memory 420 may include various types of memory, each optimized for different memory usages. For example, in some embodiments, the graphical processing device memory includes global memory, constant memory, and texture memory. Parallel portions of an application may be executed on the platform 400 as "device kernels" or simply "kernels." A kernel comprises parameterized code configured to perform a particular function. The parallel computing platform is configured to execute these kernels in an optimal manner across the platform 400 based on parameters, settings, and other selections provided by the user. Additionally, in some embodiments, the parallel computing platform may include additional functionality to allow for automatic processing of kernels in an optimal manner with minimal input provided by the user.

The processing required for each kernel is performed by a grid of thread blocks. Using concurrent kernel execution, streams, and synchronization with lightweight events, the platform 400 of FIG. 4 (or similar architectures) may be used to parallelize various operations involved with solving the computational model. The graphical processing device 410 includes one or more thread blocks 430 which represent the computation unit of the graphical processing device. The term thread block refers to a group of threads that can cooperate via shared memory and synchronize their execution to coordinate memory accesses. For example, in FIG. 4, threads 440, 445 and 450 operate in thread block 430 and access shared memory 435. Depending on the parallel computing platform used, thread blocks may be organized in a grid structure. A computation or series of computations may then be mapped onto this grid. For example, in embodiments utilizing CUDA, computations may be mapped on one-, two-, or three-dimensional grids. Each grid contains multiple thread blocks, and each thread block contains multiple threads. For example, in FIG. 4, the thread blocks 430 are organized in a two dimensional grid structure with m+1 rows and n+1 columns. Generally, threads in different thread blocks of the same grid cannot communicate or synchronize with each other. However, thread blocks in the same grid can run on the same multiprocessor within the GPU at the same time. The number of threads in each thread block may be limited by hardware or software constraints.

Continuing with reference to FIG. 4, registers 455, 460, and 465 represent the fast memory available to thread block 430. Each register is only accessible by a single thread. Thus, for example, register 455 may only be accessed by thread 440. Conversely, shared memory is allocated per thread block, so all threads in the block have access to the same shared memory. Thus, shared memory 435 is designed to be accessed, in parallel, by each thread 440, 445, and 450 in thread block 430. Threads can access data in shared memory 435 loaded from device memory 420 by other threads within the same thread block (e.g., thread block 430). The graphical processing device memory 420 is accessed by all blocks of the grid and may be implemented using, for example, Dynamic Random-Access Memory (DRAM).

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

The invention claimed is:

1. A method for computing image-derived biomarkers, the method comprising:
   receiving image data defining a three-dimensional image volume representative of an anatomical region of interest and comprising a plurality of voxels;
   applying an intensity model on a per-voxel basis across the three-dimensional image volume to assign a weighting value for each voxel indicating a likelihood that the voxel includes anatomical features related to a biomarker of interest, wherein the intensity model is a machine learning model trained using intensity features of previously acquired image data; and
   deriving information related to the biomarker of interest without prior creation of a segmented mesh from the image data by performing one or more modeling computations directly on the image data, wherein the weighting values are used to limit the modeling computations to voxels comprising the anatomical features related to the biomarker of interest.

2. The method of claim 1, further comprising:
generating an approximate segmentation of the anatomical region of interest based on results of performing the one or more modeling computations.

3. The method of claim 2, wherein the approximate segmentation is a binary mask.

4. The method of claim 2, wherein the approximate segmentation is a gray-level mask representative of segmentation accuracy for the anatomical region of interest.

5. The method of claim 2, wherein the approximate segmentation comprises a probability of particular pixels in the three-dimensional image volume belonging to the anatomical region of interest.

6. The method of claim 2, further comprising:
using the approximate segmentation to iteratively perform the one or more modeling computations directly on the image data to derive information related to the biomarker of interest.

7. The method of claim 6, further comprising:
refining the approximate segmentation during each iteration based on results of the one or more modeling computations.

8. The method of claim 1, wherein the anatomical region of interest comprises cardiac vascular structure and the one or more modeling computations provide a measure of fluid dynamics within the cardiac vascular structure.

9. The method of claim 8, wherein the measure of fluid dynamics is pressure difference within the cardiac vascular structure.

10. The method of claim 8, wherein the measure of fluid dynamics is fractional flow reserve within the cardiac vascular structure.

11. A method for computing image-derived biomarkers, the method comprising:
receiving image data comprising a plurality of voxels defining a three-dimensional image volume representative of an anatomical region of interest and comprising a plurality of voxels;
determining an anatomical structure related to a biomarker of interest;
selecting an intensity model based on the anatomical structure related to the biomarker of interest, wherein the intensity model is a machine learning model trained using intensity features of previously acquired image data;
applying the intensity model on a per-voxel basis across the three-dimensional image volume to determine a weighting value for each voxel indicating a likelihood that the voxel includes a portion of the anatomical structure; and
deriving information related to the biomarker of interest without prior creation of a segmented mesh from the image data by performing one or more modeling computations directly on the image data, wherein the weighting values are used to limit the modeling computations to voxels comprising the anatomical features related to the biomarker of interest.

12. The method of claim 11, wherein determining the anatomical structure related to the biomarker of interest comprises:
receiving user input defining a medical condition; and
selecting the anatomical structure and the biomarker of interest based on the medical condition.

13. The method of claim 11, wherein the intensity model is selected based on a database of past history from other patients and annotated models for how different intensity values correspond to presence of the anatomical structure.

14. The method of claim 11, further comprising:
determining one or more study-specific input values defining seed points for the intensity model,
wherein the intensity model uses the one or more study-specific input values in determining the plurality of weighting values.

15. The method of claim 14, wherein the one or more study-specific input values are automatically selected based on previous studies related to the anatomical structure.

16. The method of claim 14, wherein the one or more study-specific input values are determined based on user input via a graphical user interface (GUI).

17. The method of claim 11, further comprising:
generating an approximate segmentation of the anatomical structure based on results of applying the computational model to the image data.

18. The method of claim 17, wherein the approximate segmentation is a binary mask.

19. The method of claim 17, wherein the approximate segmentation is a gray-level mask representative of segmentation accuracy for the anatomical region of interest.

20. The method of claim 17, further comprising:
using the approximate segmentation to iteratively apply the computational model to the image data; and
refining the approximate segmentation during each iteration based on results of applying the computational model to the image data.

21. A system for computing image-derived biomarkers, the system comprising:
a scanner device configured to acquire image data defining a three-dimensional image volume representative of an anatomical region of interest and comprising a plurality of voxels; and
a computer operably coupled to the scanner device and configured to:
apply an intensity model to assign a weighting value for each voxel indicating a likelihood that the voxel includes anatomical features related to a biomarker of interest, wherein the intensity model is a machine learning model trained using intensity features of previously acquired image data, and
derive information related to the biomarker of interest without prior creation of a segmented mesh from the image data by performing one or more modeling computations directly on the image data, wherein the weighting values are used to limit the modeling computations to voxels comprising the anatomical features related to the biomarker of interest.

* * * * *